United States Patent [19]

Travis

[11] Patent Number: 5,229,295
[45] Date of Patent: Jul. 20, 1993

[54] METHOD FOR TESTING GASOLINE FOR WATER AND ALCOHOL IN THE PRESENCE OR ABSENCE OF THE OTHER

[76] Inventor: Basil B. Travis, P.O. Box 287, Lodi, Calif. 95241

[21] Appl. No.: 862,201

[22] Filed: Apr. 2, 1992

[51] Int. Cl.⁵ .................... G01N 33/18; G01N 33/22
[52] U.S. Cl. ........................................ 436/39; 436/40; 436/60; 436/166
[58] Field of Search ............... 436/39, 40, 166, 60

[56] References Cited

U.S. PATENT DOCUMENTS

| | | | |
|---|---|---|---|
| 2,950,958 | 8/1960 | Nesh | 436/40 |
| 3,341,298 | 9/1967 | Pietrangelo | 436/40 |
| 3,528,775 | 9/1970 | O'Hara et al. | 436/40 |
| 3,833,340 | 9/1974 | Jones et al. | 23/230 HC |
| 4,578,357 | 3/1986 | Melpolder | 436/39 |
| 4,617,278 | 10/1986 | Reed | 436/60 |
| 4,717,671 | 1/1988 | Melpolder | 436/39 |
| 4,962,039 | 10/1990 | Benedyk | 436/40 |

OTHER PUBLICATIONS

The Merck Index, 10th Ed., 1983, pp. 627-628 & 1231.

*Primary Examiner*—James C. Housel
*Assistant Examiner*—Milton I. Cano
*Attorney, Agent, or Firm*—Basil Travis

[57] ABSTRACT

An environmentally compatible method for field testing gasoline, and other liquid hydrocarbons, for the presence of water and/or alcohol in the presence or absence of the other utilizing colorimetric reagents comprising methylene blue dye, anhydrous sodium borate and gentian violet dye in suspension with mineral oil. When alcohol is present a volumetric test using dilute nitric acid is further described to measure its percentage in the fuel.

3 Claims, 2 Drawing Sheets

METHOD FOR TESTING GASOLINE FOR WATER AND ALCOHOL IN THE PRESENCE OR ABSENCE OF THE OTHER

BACKGROUND OF THE INVENTION

1. Field of the Invention

The present invention generally concerns both colorimetric detection of water and alcohol in gasoline, but also includes a volumetric determination of alcohol if present in fuels commonly known as "gasohols." Additionally, the tests are also applicable to a variety of liquid hydrocarbons for detection of water and/or alcohol therein. Moreover, they are believed environmentally safe.

2. Prior Art

Alcohol is fastly becoming a familiar component of gasolines known as gasohols wherein the alcohol content is often found to be as much as 10%, and in some specialty fuels it can approach nearly 100%. Although ethanol is most often the alcohol of choice, other alcohols such as methanol or tertiary butanol are sometimes added to gasoline or even used as fuels themselves for various reasons. In this regard the propensity of alcohols to absorb water from the environment has long been known where it is theoretically possible to find as much as 10% disbursed water in alcohol which would translate into about 1% water disbursed in gasohols containing 10% alcohol. The adverse effects of excessive water in a fuel system cannot be overstated as ranging from corrosion to poor engine performance, and accordingly over the past 30 years of prior art in the field there have been various methods described for detecting water and/or alcohol in engine fuels.

For example, in U.S. Pat. No. 2,968,940 (1961), Feldman, et. al., describes a method to detect 30 parts per million disbursed water in jet aircraft fuels (the "go-no go" limit) by adding one-half gram of a mixture of sodium o-cresolsulfonphthalien and barium carbonate to 100 cc's of jet fuel, shaking it, allowing the powder to settle and noting its color. Although several common additives were found not to interfere, none of these included alcohols in the concentration normally found in gasohols.

In U.S. Pat. No. 3,505,020 (1970), Caldwell, et. al., discloses an improved mixture of methylene violet or fuchsia (3-amino-7(dimethylamino)-5-phenyl-phenazinium chloride) and an absorbent from the Group II metals, such as calcium carbonate, to detect 30 parts per million disbursed water in jet fuels but without reference to the presence or absence of alcohol therein.

In U.S. Pat. No. 4,070,154 (1978), Mascher, et. al., discloses a colorimetric test for as little as 0.1% alcohol in jet aircraft fuels (the ice formation inhibitors) by an emulsion reagent of sodium vanadiate, 8-hydroxyquinoline, water, acetic acid and an organic solvent. Because water is part of his reagent it was not intended to detect water in the fuel.

In U.S. Pat. No. 4,608,345 (1986), Feldman, et. al., describes a colorimetric test for detecting small amounts (1%) of alcohol in gasoline using a variety of alcohol soluble-hydrocarbon insoluble dyes with an absorbent from the Group II metals, such as calcium carbonate, however since the absorbent is non-selective, water must first be removed from the fuel by treating with a drying agent.

In U.S. Pat. No. 4,676,931 (1987), I first proposed forming colored hydrates to detected disbursed water in fuels by adding an anhydrous powder which, when shaken with the fuel, would remove only the water so that the presence of alcohol would not interfere with the test. The preferred anhydrous powder was cupric sulfate because it formed two colored-hydrated crystals, light blue and dark blue, depending upon the amount of water present, however a few problems were found using this test under actual field conditions.

First, it was found very difficult to measure a small amount of the powder into a test vial in the field. Secondly, it was also nearly impossible to keep the anhydrous powder dry because every time its container was opened the powder absorbed water vapor from the air and became discolored prior to use. Thirdly, a relatively large fuel sample was required for enough sensitivity where disposal of the sample after the test became increasingly difficult with the advent of environmental regulations. And lastly, the formation of the blue hydrated crystals was always somewhat masked by the usual yellowish hue of various fuels. Accordingly, and in view of the above problems, it was felt that a method be developed that would specially detect water and/or alcohol in the presence or absence of the other with smaller fuel samples of about five cc's to facilitate their easy disposal with relatively safe and inexpensive chemicals. The present invention addresses that need.

SUMMARY OF THE INVENTION

Three chemical reagents, their formulations and uses are disclosed to test gasoline for water and alcohol in the presence or absence of the other, and if alcohol is present the method further provides a simple volumetric test to determine the amount of alcohol present in the fuel. Only small samples of fuel (approx. 5 cc's) need be tested to allow their easy disposal pursuant to environmental concerns, and only small amounts of relatively harmless chemicals comprising methylene blue dye, gentian violet dye, anhydrous sodium borate, mineral oil and dilute nitric acid (less than 10% in strength) are used in the method along with re-usable glass test vials, all of which post no known hazard to the environment. These easy to use and readily interpretable tests make them ideal for use in the field because the reagents are forever stable, storable and usable under extreme weather conditions, and readable by flashlight in darkness.

A colorimetric reagent is used for detecting water is a suspension of 0.1% methylene blue-2% anhydrous sodium borate in mineral oil for easy dispensing from plastic dropper bottles, while preserving anhydrous integrity of the reagent, and the test for water may be carried out in a clear glass vial preferably with screw cap so that approximately 2 cc's of fuel need only be vigorously shaken with approximate 5 drops of the reagent for production of a color easily observed in the vial and compared against a color chart if necessary, or since the test result is stable, the test vial may itself be kept as a record of the test.

A colorimetric test for alcohols (any alcohol) comprises 0.1% gentian violet dye in mineral oil suspension which when shaken with fuel causes the fuel to become purple when there is at least 1% alcohol present. The purple color is proportional to the alcohol concentration in the range 1% to 5% where the percentage of alcohol may be estimated by the intensity of the purple color. However, as is often the case, where more than 5% alcohol is found in gasohols, a volumetric measurement is required to determine its percentage.

A volumetric test for alcohol uses a water solution of approximately 9% nitric acid reagent and an especially designed calibrated test vial of approximately 7 cc's capacity with graduations from zero to 100. To perform the test about 1 cc of the nitric acid reagent is filled to the zero mark and then fuel is added to the 100 mark on the test vial. A screw cap is preferably placed on the vial, the vial shaken and the layers therein allowed to separate at which point the percentage of alcohol is indicated by the graduations.

DESCRIPTION OF THE PREFERRED EMBODIMENTS

1. Colorimetric Test for Water

Figure 1:
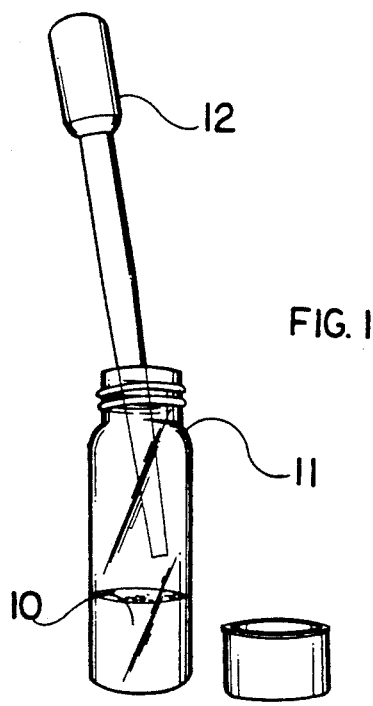
FIG. 1 illustrates a preferred 1 dram-type test vial being filled with approximately 2 cc's of gasoline for colorimetric testing for the presence of either water or alcohol.

A. Preparation of Water Test Reagent i. Anhydrous Sodium Borate

As previously discussed in the Prior Art section above, the detection of disbursed water in fuel by colorimetric methods requires in every case that the water first be separated from the fuel by some physical or chemical means, such as an absorbent or by forming some type of crystalline hydrate so as to concentrate the disbursed water onto a relatively small volume whereon a water soluble dye may react and can be observed. Anhydrous sodium borate was found to be the preferred compound of choice in the present invention for several reasons. First, it is not a Group II Metal as claimed in the prior art nor is it mentioned as an absorbent for water in fuels. Secondly, it is inexpensive, non-toxic and readily forms white hydrates upon which methylene blue dye attaches to give the hydrated crystals a vivid blue color insoluble in fuel and easily readable with the naked eye. Thirdly, anhydrous sodium borate is easily made from common "Borax" by placing Borax in a conventional kitchen oven at 150 degrees centigrade for one hour or until the powder appears to take on a slight violet hue indicating that the water has been driven off. When allowed to cool it is fairly stable from the moisture in the air if kept in a closed container, such as a Mason jar.

ii. Methylene Blue Dye

Methylene blue dye or 3,7-bis(dimethylaminol)-phenazothionium chloride is a commonly used biological stain and relatively inexpensive. It should be distinguished as a separate chemical compound altogether than Methyl Violet as claimed in the prior art, although both dyes are known to be water soluble-hydrocarbon insoluble, methylene blue preferably attaches to hydrated borate in the presence of alcohol in gasohols, and moreover, methylene blue has not been utilized in the prior art as a test for water in the presence of alcohol when in a mineral oil suspension with anhydrous sodium borate.

iii. Mineral Oil Suspension of 2% Anhydrous Sodium Borate & 0.1% Methylene Blue Dye.

Accordingly, and what is believed to be a new, novel and non-obvious improvement over all prior art colorimetric methods for detecting water in fuels is the unique combination of anhydrous sodium borate with methylene blue powder in a suspension of mineral oil. Since the purpose of mineral oil is to merely provide a hydrocarbon-soluble medium for the chemical reaction while at the same time preventing entrance of atmospheric moisture, any inexpensive mineral oil available at the local drug store should suffice. It appears important, however, that the initial mixing of mineral oil with the dry borate and dye be done in some sort of blender such as a common juice blender for several minutes so that the resulting powder particles are of somewhat uniform size and evenly distributed throughout the mineral oil before filling a reagent bottle. For example, if a pint of the test reagent is to be prepared (500 cc's) it can be conveniently done in a common juice blender by simply pouring a pint of mineral oil into the blender with one-half gram of methylene blue dye and one gram of anhydrous sodium borate, turning on the blender for about five minutes and then while in suspension, simply pouring it into dispensing bottles, such as plastic dropping bottles wherein the reagent is not only stable but can be easily dispensed into fuel after shaking it.

B. Performing the Test for Water

As it may be perhaps obvious in the prior art tests for water, sensitivity of a test largely depends on the sample size. For example, 100 cc's of fuel is often required to detect 30 parts per million water and it logically follows that the sensitivity of a colorimetric test can usually be increased with a larger sample size which is the case with the test of the present invention. But from a practical standpoint more than 30 parts per million water will often be found in gasohols so that a much smaller sample only need be tested.

FIG. 1 illustrates about 2 cc's of fuel 10 being placed into a test vial 11 by means of a plastic dropper 12. This quantity is about one-fiftieth of the amount usually used for colorimetric tests and likewise the sensitivity of the test has decreased as well. However, it was found in actual practice that where there were problems with gasohols that caused corrosion or affected engine performance, the water content approached 1000 parts per million or 0.1% which is the minimal detectable limit of the present test, but of course its sensitivity can always be increased by using a larger sample of fuel.

As an example, if one needed to detect 30 parts per million water in gasohol it would be within the scope and spirit of the present invention to use 100 cc's or perhaps even 1,000 cc's of fuel with 5 or more drops of the preferred reagent because the principle of the test would remain the same, but the disposal problem would greatly increase. Thus, it is believed another advantage of the present invention over the prior art that a smaller sample of fuel can be used to conform to environmental concerns.

Figure 2:
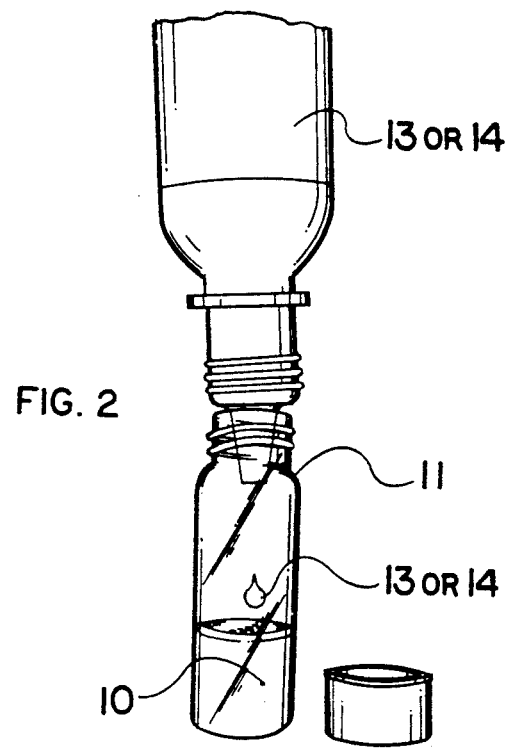
FIG. 2 shows the addition of about 5 drops of a mineral oil reagent suspension (previously shaken) to gasoline sample in the test vial.

FIG. 2 shows the addition of about 5 drops of water test reagent 13 to a test vial 11, however since the reagent is a suspension it must be shaken prior to use so as to disburse its borate-dye particles throughout the mineral oil. Because the reagent 13 when thoroughly mixed is approximately 2% anhydrous sodium borate plus 0.1% methylene blue dye, it can be easily calculated that 5 drops (¼ cc) will deliver about 20 milligrams of the borate plus 1 milligram of the dye to the fuel sample 10 in the test vial 11.

Figure 3:
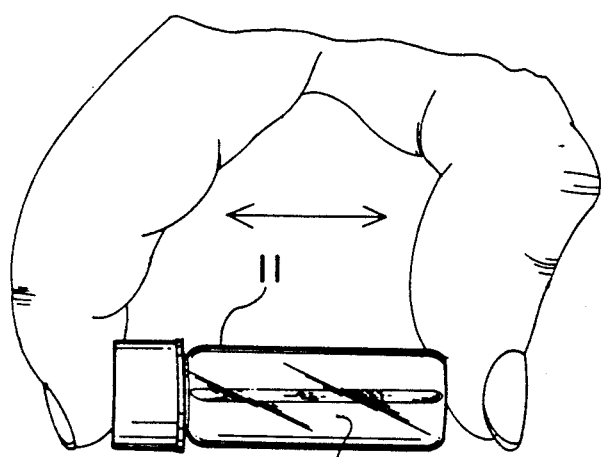
FIG. 3 illustrates shaking the test vial to mix the gasoline sample with a colorimetric reagent.

FIG. 3 illustrates the preferred way to mix the fuel sample 10 with water reagent 13 in a test vial 11 by vigorously shaking for about 5 seconds. Because only a small fuel sample is used (2 cc's) it is important that said 20 milligrams of borate be given the opportunity to contact all of the disbursed water in the fuel 10 so that the water can be absorbed for the dye to react. For example, if a fuel 10 was to contain, say, 1000 parts per million water, it would follow that only 2 milligrams of water would be present in 2 cc's of fuel so it is understandable that adequate mixing of fuel is necessary for the borate to absorb the disbursed water therein.

Figure 4:
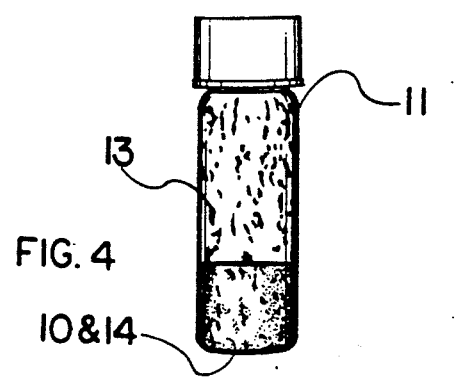
FIG. 4 depicts a typical colorimetric test result as seen by a color inside the test vial.

FIG. 4 shows test results when more than 1000 parts per million water is present in fuel 10. The usual result is that blue reagent 13 particles adhere to the inside of the test vial 11 and are easily observable through the glass, which is another improvement over the cited prior art wherein, for example, the color of insoluble powder precipitate needed to be observed within the fuel 10.

Using the quantities of fuel 10 and reagent 13 of the preferred embodiment, there will be no detectable reaction, e.g., no blue reagent on the glass, where the fuel sample contains less that 1000 parts per million water, and any powder observed after the test will appear white at the bottom of the test vial 11.

As previously mentioned, this test is not affected by alcohol in the fuel, if any, because most alcohols do not form hydrates with borate thereby making the test particularly ideal for gasohols. However, it should pointed out here that the test is not limited to gasohols nor is it limited to gasolines as it can be also used to test any hydrocarbon fuel such as diesel fuel or even industrial solvents which are water insoluble such as liquid halogenated hydrocarbons.

2. Colorimetric Test for Alcohol

A. Preparation of Colorimetric Alcohol Test Reagent 0.1% Gentian Violet Dye in Mineral Oil As it is perhaps well known, gentian violet dye is chemically methylrosaniline chloride and has been used as both a bacteriological and histological stain, in internal medicine to treat some fluke infections and topically as an antibacterial and antifungal agent. It is also commonly used in veterinarian medicine and has classically been utilized in law enforcement for detection of criminal activities, namely by application of fire alarm boxes to identify those persons who turn in false alarms. Because it is virtually water insoluble, gentian violet dye is nearly impossible to remove from the skin with soap and a scrub brush thereby making it useful to identify criminals. However, gentian violet dye is also very soluble in common alcohols but virtually insoluble in gasoline, including various liquid hydrocarbon fuels, thusly making it ideal for detection of alcohol in gasoline, whether water is present or not. Accordingly, the use of gentian violet dye is believed another improvement over the cited prior art because it has not been heretofore utilized by itself nor in suspension with mineral oil for alcohol detection.

Because gentian violet dye is also insoluble in mineral oil it need be placed in suspension preferably with a common juice blender, as previously described, wherein, for example, 500 cc's of mineral oil plus about one-half gram of said dye should be blended for about 5 minutes to achieve uniform particle size while also suspending the dye for dispensing the suspension into reagent bottles, such as plastic dropping bottles for use in the field.

B. Performing the Colorimetric Test for Alcohol

Reference is once again made to FIGS. 1 & 2 to illustrate about 2 cc's of fuel 10 being added to a typical test vial 11 where the illustration in FIG. 2 shows the addition of about 5 drops of alcohol test reagent 14 in a manner previously discussed, however said reagent 14 must be shaken prior to the test for uniform distribution of the dye particles throughout the mineral oil so that by adding 5 drops of the suspension there will be delivered about 1 milligram of gentian violet dye into the fuel 10.

Referring again to FIG. 3, there is shown mixing of fuel 10 with alcohol reagent 14 in a test vial 11 by vigorously shaking for about 5 seconds. It has been found experimentally that 1 milligram of gentian violet dye will detect a minimum of 1% alcohol in a 2 cc fuel sample, and it naturally follows that a lesser amount of alcohol may accordingly be detected with a greater fuel sample. However, in actual practice the need for an alcohol test has only arisen where there were larger amounts, rather than smaller amounts, of alcohol in fuels, therefore the preferred detection limit of 1% has been satisfactory for field testing.

It should be remembered at this point that one of the primary goals of the present invention is to minimize both the sample size and quantity of reagents used in the test in respect for environmental concerns which has not been addressed in the prior art and believed to be an improvement thereof because not only 2 cc's (approx. 40 drops) of fuel need be tested but also only 1 milligram quantities of medically acceptable dyes require disposal.

FIG. 4 also illustrates the results of a typical test for alcohol where the alcohol reagent 14 causes the fuel 10 in a test vial 11 to become a discernable purple color if at least 1% alcohol is present. It has been found in actual practice that the intensity of the purple color is proportional to the concentration of alcohol in fuel between 1% and 5% wherein said range a color chart may be prepared and utilized to estimate the concentration of alcohol with fair accuracy, however since where said color indicates 5% or more alcohol a volumetric test should be preformed as conformation because the purple color produced by gentian violet dye is too intense to distinguish with the naked eye. Therefore, a volumetric test is further described as necessary for a complete disclosure of the present invention.

3. Volumetric Test for Alcohol

A. Preparation of Alcohol Volumetric Test Reagent

9% aqueous nitric acid

Nitrates have been known in analytical chemistry to react with alcohols, especially ceric ammonium nitrate and ethanol which produces a particular color, thus it was thought possible to utilize a nitrate solution to literally extract alcohol from gasoline and measure its increased volume as an indication of the percentage of alcohol in the fuel. Ceric ammonium nitrate (20% by weight in 6% nitric acid) was found to produce the most accurate results when shaken with fuel in the approximate ratio of 1 part nitrate solution and 10 parts fuel, and the alcohol was not only completely extracted but resulted in a dark brown colored solution in the bottom part of a graduated test vessel making reading of the graduations easy. However, ceric ammonium nitrate is expensive, and accordingly various strengths of nitric acid alone were tried with a variety of known gasohol samples where it was found that 9% nitric acid itself produced just as accurate results but for a fraction of the cost. Of course 6.3% (one-normal) nitric acid or higher strengths will also extract alcohol from gasoline with various accuracies, but 9% was found optimum for relatively small quantities of fuels (less than 10 cc's) and since 9% is roughly 1.5 normal it is relatively safe and easily prepared with distilled water by diluting commercially available nitric acid.

B. Preparation of Test Vial

Normally, liquid extractions are easily done in stoppered graduated cylinders having some sort of vertical numerical scale on them which can be read with respect to the liquid level therein, and it is of course possible and perhaps even advisable to perform the volumetric test of the present invention in such a vessel if one if available. However, such cylinders are usually expensive and often far distant from a field location where a test need be done, therefore an inexpensive glass vial is described as a preferred vessel in which to perform the test.

As it was previously said about sensitivity being related to sample size, so too is accuracy. In other words, one would expect greater accuracy from a larger fuel sample simply because its volume in a graduated cylinder could be more accurately read. However, as also previously emphasized, disposal of a large test sample is difficult so some balance need be struck between accuracy and disposability. Accordingly, it was experimentally determined that approximately 6 cc's of fuel when shaken with 1 cc of 9% nitric acid would efficiently extract all of the alcohol into the dilute acid thereby resulting in a change of their respective volumes which is readable with fair accuracy. Obviously narrower vials that contains 7 cc's volume provide greater accuracy with respect to their vertical scale graduations but at the same time a vial should be wide enough to easily accommodate adding of reagent and sample in the field.

The preferred type of vial used in this test is a 2-dram No. L-915 clear glass screw cap vial manufactured by Acme Vial & Glass Co. in Paso Robles, Calif., as illustrated in FIGS. 5 through 8, however it is not sold with a graduated scale. Therefore, a graduated scale need be prepared.

To prepare the scale it briefly need be recalled that the ratio of dilute nitric acid reagent to fuel is 1 plus 6, e.g., 1 cc reagent plus 6 cc's fuel for a total of 7 cc's capacity. Of course one may use 10+60 for a total of 70 cc's in a larger vessel, and so forth, where greater accuracy is needed, but 7 cc's will provide a result within a few % error which is sufficient for field work. But regardless of the style of vial selected for the test it should be first calibrated with a graduated scale to measure the qualities of particular volumes used.

To establish the scale first add 1 cc (20 drops) of dilute nitric acid reagent to a test vial and then mark by a file scratch or with marking pen the position of the top of said reagent in said vial calling it "0". Next, put 6 times the amount (6 cc's) of fuel into the test vial and mark the position of the top of the fuel as "100". Measure with a metric ruler the distance between the marks making one-half way "50", and the respective distances between those marks "25" and "75" and so on until a vertically linear scale is established on the exterior of the vial or upon a thin vertical strip of adhesive labeling thereon where the numbers represent the percent of alcohol in the fuel after the test.

C. Performing the Volumetric Test for Alcohol

Figure 5:
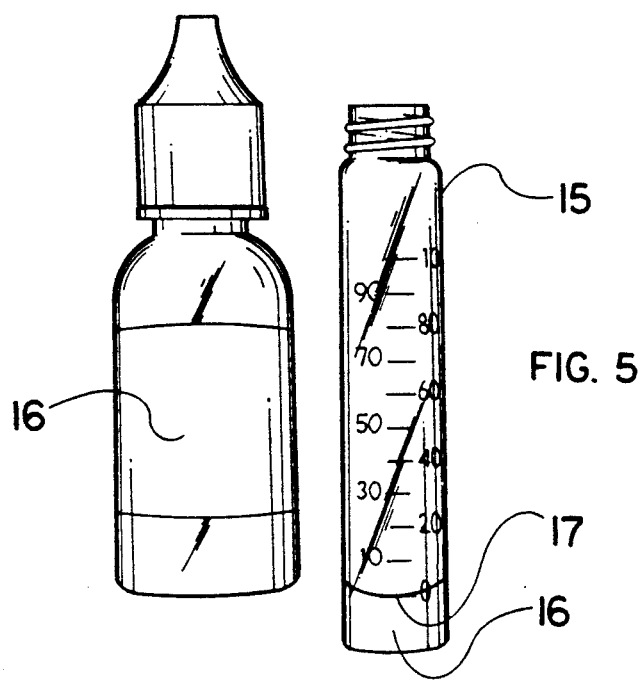
FIG. 5 illustrates a volumetric test for determining the percentage of alcohol in a fuel using a calibrated test vial, as shown filled to its zero mark with dilute nitric acid reagent.

FIG. 5 shows a calibrated test vial 15 of the present invention filled to the zero mark with dilute nitric acid test reagent 16. In this illustration it is important to note that the bottom point of the meniscus 17 rests directly on the zero line because the accuracy of the test greatly depends on the accurate measurement of this small volume.

Figure 6:
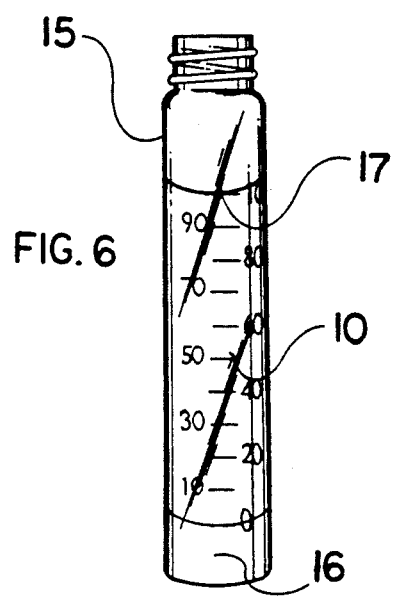
FIG. 6 shows the calibrated test vial filled to the 100% mark with fuel.
Figure 7:
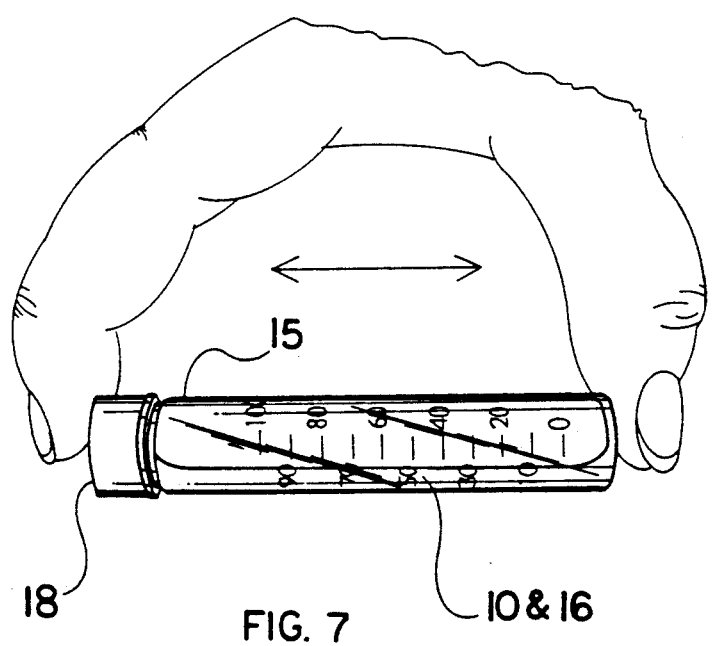
FIG. 7 shows shaking the calibrated test vial to extract alcohol from the fuel by the reagent.

FIG. 6 illustrates the test vial 15 filled to the 100% mark with fuel 10 and once again it should be noted that the bottom of the meniscus 17 rests upon the top graduation. A cap 18 is placed on the vial 15 and it is shaken vigorously as depicted in FIG. 7 for about 5 seconds causing the dilute nitric acid reagent 16 to contact and extract alcohol, if any, from the fuel 10.

Figure 8:
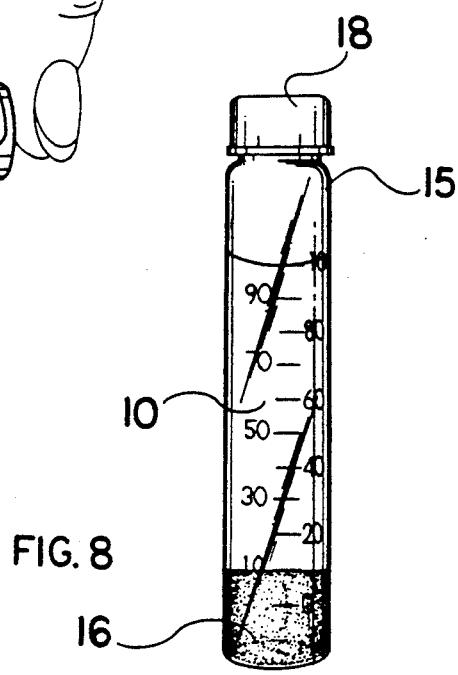
FIG. 8 depicts the results of a volumetric test with a fuel containing 10% alcohol.

FIG. 8 shows a test result where the fuel contained 10% alcohol as indicated at the point of separation of liquids in the test vial 15 on the "10" line. Additionally, it will be also noted that the previously colorless dilute nitric acid reagent 16 has now become dark in color which is believed caused by bonding of alcohol with the nitrate ion in the lower aqueous solution thereby also making it easy to read the graduated scale.

Having described my invention with particularity, I claim:

1. A method for detecting the presence of water in fuels from a chemical color reaction comprising the steps of:
   A. preparing a suspension of approximately 2% anhydrous sodium borate plus 0.1% methylene blue dye in mineral oil;
   B. contacting said suspension with a sample of fuel to be tested;
   C. reacting any water in said sample of fuel with said suspension to produce a color change; observing said color change if water is present in said fuel, wherein said fuels comprise liquid hydrocarbon fuel.

2. A method for detecting the presence of alcohols in fuels from a chemical color reaction comprising the steps of:
   A. preparing a suspension of approximately 0.1% gentian violet dye in mineral oil;
   B. contacting said suspension with fuel to be tested;
   C. reacting any alcohol in said sample of fuel with said suspension to produce a color change; observing said color change if alcohol is present in said fuel, wherein said fuels comprise liquid hydrocarbon fuel.

3. A method for measuring the amount of alcohol in fuels from a chemical extraction comprising the steps of:

A. preparing an aqueous solution consisting of 9% nitric acid;
B. preparing a test vial with a graduated numerical scale thereon;
C. contacting fuel to be tested with said nitric acid solution in said test vial;
D. observing the percentage of alcohol if present in the fuel on said graduated numerical scale by result of a change in their respective volumes resulting in the formation of a dark colored solution being readable in the bottom part on said scale; wherein said fuels comprise liquid hydrocarbon fuel.

* * * * *